United States Patent [19]

Hendrix et al.

[11] Patent Number: 5,391,352
[45] Date of Patent: Feb. 21, 1995

[54] BLOOD ANALYSIS APPARATUS

[76] Inventors: Billy E. Hendrix, 5106 Foxbridge Cir., Clearwater, Fla. 34260; Kurt H. Myrmel, 5430 Worthington Loop, Palm Harbor, Fla. 34685

[21] Appl. No.: 117,412
[22] Filed: Sep. 7, 1993
[51] Int. Cl.⁶ .................................... G01N 21/00
[52] U.S. Cl. .............................. 422/65; 422/63; 422/67; 422/68.1; 422/73; 422/102; 436/47; 436/164; 436/165; 356/39; 356/246
[58] Field of Search ............ 436/70, 164, 165, 47; 422/102, 101, 65, 67, 68.1, 73, 63; 356/246 X, 39, 432, 436, 440

[56] References Cited

U.S. PATENT DOCUMENTS

| | | | |
|---|---|---|---|
| 3,718,439 | 2/1973 | Rosse et al. | 23/259 |
| 3,994,594 | 11/1976 | Sandrock et al. | 356/246 |
| 4,251,159 | 2/1981 | White | 356/246 |
| 4,429,373 | 1/1984 | Fletcher et al. | 422/67 |
| 4,451,433 | 5/1984 | Yamashita et al. | 422/67 |
| 4,580,895 | 4/1986 | Patel | 356/39 |
| 4,729,661 | 3/1988 | Bell | 356/246 |

Primary Examiner—Donald E. Czaja
Assistant Examiner—Lien Tran
Attorney, Agent, or Firm—Michael J. Colitz, Jr.

[57] ABSTRACT

A system for analyzing a sample of fluid for a plurality of characteristics comprising a cuvette with a plurality of chambers for fluid to be analyzed; a housing assembly having a frame and a support subassembly reciprocable with respect to each other, the support subassembly including a base to receive the cuvette; and processing mechanisms associated with the housing assembly including a first component to intermix the fluid with a diluent and then with reagents in the chambers to facilitate the analysis thereof, the processing mechanisms further including a light source and an associated sensor located in an operative relationship with respect to the cuvette and a computer operatively associated with the sensor to determine a plurality of characteristics of the fluid within the chambers.

2 Claims, 4 Drawing Sheets

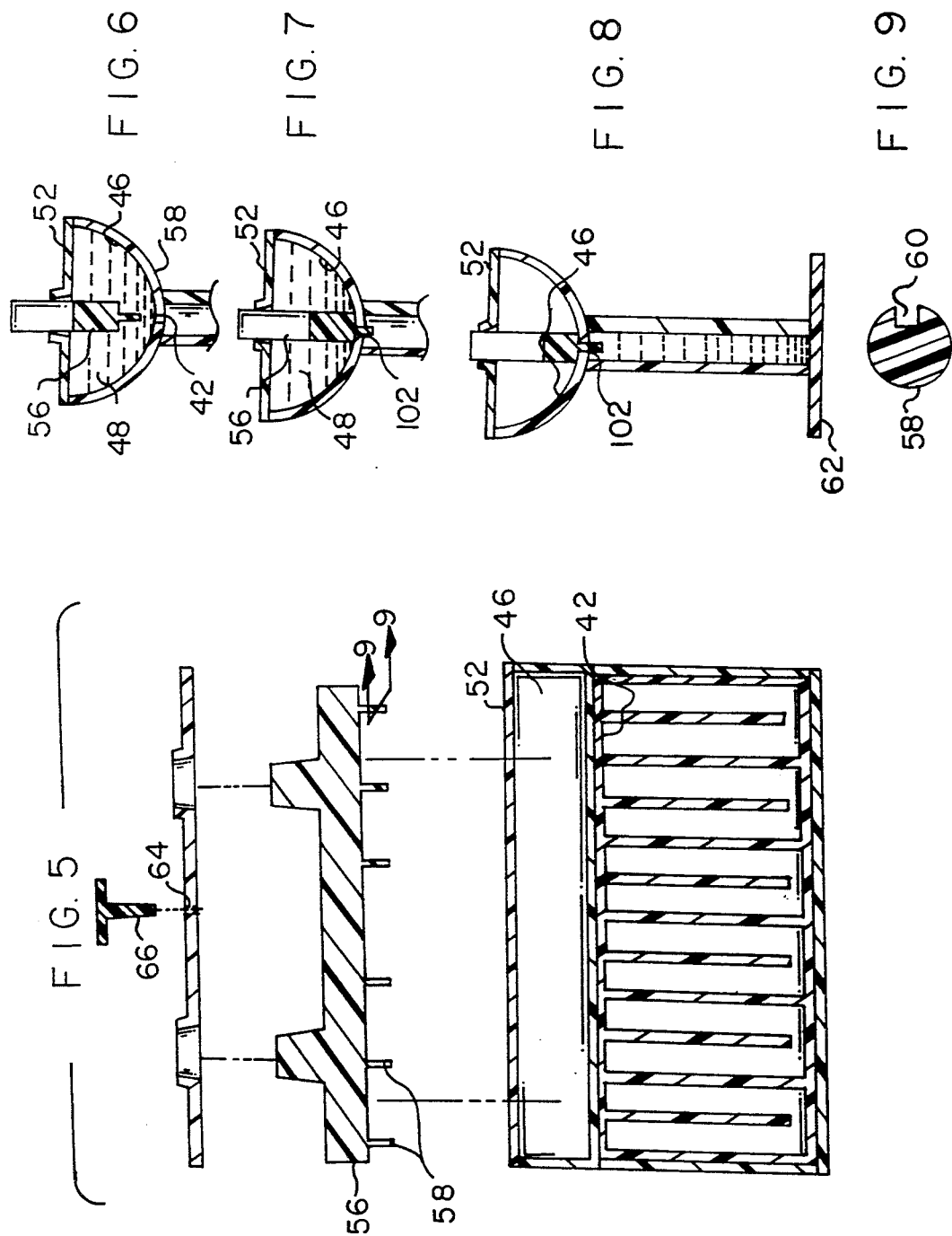

4,391,352

BLOOD ANALYSIS APPARATUS

BACKGROUND OF THE INVENTION

1. Field of the Invention

This invention relates to a blood analysis apparatus and method and, more particularly, to a method and system for analyzing a sample of blood for a plurality of characteristics.

2. Description of the Background Art

Many types of blood analysis apparatuses and methods are known and are in wide use today throughout the medical industry. Such known and used methods and apparatus for blood analysis are generally less than sufficient in terms of accuracy, speed and cost. By way of example, there is simply nothing known which will analyze a sample of blood for a plurality of characteristics. There is nothing known which will rapidly analyze a large number of blood samples, analyzing each sample for a large number of characteristics. And there is nothing in the prior art to analyze blood samples with an optimum of accuracy, rapidness and cost effectiveness, all with convenience of use and with foolproof equipment.

By way of example, typical examples of blood analyzers are described in the patent literature. Nota U.S. Pat. No. 4,865,413 to Leon; 5,132,233 to Jackson, and 5,186,396 to Bach. Of these patents, Leon discloses a cuvette defining four reagent chambers. The chambers contain reagents therewithin. Four separate tests can be performed on a test sample simultaneously.

Other patent disclosures less pertinent than the above-described three include U.S. Pat. Nos. 4,767,600 to Vicario; 5,176,880 to Iwasaki and 5,192,509 to Surjaatmadja.

No prior blood analysis apparatus, however, has the capability to analyze a sample of blood for a plurality of characteristics as does the present invention.

Accordingly, it is an object of the present invention to provide a method and system for analyzing a sample of fluid for a plurality of characteristics comprising a cuvette with a plurality of chambers for fluid to be analyzed; a housing assembly having a frame and a support subassembly reciprocable with respect to each other, the support subassembly including a base to receive the cuvette; and processing mechanisms associated with the housing assembly including first means to intermix the fluid with a diluent and then with reagents in the chambers to facilitate the analysis thereof, the processing mechanisms further including a light source and an associated sensor located in an operative relationship with respect to the cuvette and computer means operatively associated with the sensor to determine a plurality of characteristics of the fluid within the chambers.

A further object of the invention is to analyze a sample of blood for a plurality of characteristics.

A further object of the invention is to configure and utilize a cuvette for greater accuracy, convenience and economy.

A further object of the invention is to rapidly analyze a large number of blood samples, analyzing each sample for a large number of characteristics.

It is a further object of the invention to analyze blood accurately, rapidly and cost effectively with foolproof equipment.

These objects should be construed to be merely illustrative of some of the more prominent features and applications of the intended invention. Many other beneficial results can be obtained by applying the disclosed invention in a different manner or by modifying the invention within the scope of the disclosure. Accordingly, other objects and a more comprehensive understanding of the invention may be obtained by referring to the summary of the invention, and the detailed description of the preferred embodiment in addition to the scope of the invention defined by the claims taken in conjunction with the accompanying drawings.

SUMMARY OF THE INVENTION

The invention is defined by the appended claims with the specific embodiment shown in the attached drawings. For the purposes of summarizing the invention, the invention may be incorporated into a method and system for analyzing a sample of blood for a plurality of characteristics comprising, in combination, a plurality of cuvettes, each cuvette having a front face, a rear face, a closed lower edge, an open upper edge and parallel side walls therebetween, thereby providing a lower volume, a plurality of long divider members located at spaced locations between the front and rear faces and top and bottom walls to divide up the cuvette into a plurality of separate chambers, each chamber having an intermediate short divider member extending downwardly from the upper edge to a location above the lower edge thereby forming the chambers into essentially U-shaped chambers, a first horizontal sheet extending across the spacers between the front and back faces and side walls to seal the chambers one with respect to the other, each chamber supporting a vacuum with a different reagent therein, a second horizontal sheet above the first horizontal sheet to form a horizontal reservoir with a fluid diluent positioned between the horizontal sheets to overlie the chambers, a plate within the reservoir with downwardly directed pins at spaced points corresponding to the spaced chambers whereby downward movement of the plate and pins will puncture the first horizontal sheet and allow the flow of fluid from the horizontal chamber into the vertical chamber for reacting with the reagents, the lower extent of the cuvette having a horizontal support for being supported by a base, the second horizontal sheet also being formed with a small aperture with an associated stopper for allowing the addition of body fluids into the reservoir for analysis; a housing assembly having a fixed frame and a movable support subassembly reciprocable with respect to the frame, the frame including a base with a longitudinal slot for supporting a plurality of cuvettes in edge-to-edge relationship in a linear array and means to move the movable support subassembly with respect to the supported cuvettes in a linear path of travel; and processing mechanisms associated with the housing assembly including first means to drive the pins downwardly to form holes in the first horizontal sheet with a hole over each chamber whereby body fluids intermixed with diluent in the horizontal reservoir will be drawn into the chambers for mixing with the reagent to facilitate the analysis thereof, the processing mechanisms further including a movable fiber optic light source and an associated movable fiber optic sensor located in an operative relationship with the light source on opposite sides of the path of travel and fixed computer means operatively associated with the sensor to determine a plurality of characteristics of the fluids within the chambers, one characteristic for each chamber.

The foregoing has outlined rather broadly, the more pertinent and important features of the present invention. The detailed description of the invention that follows is offered so that the present contribution to the art may be more fully appreciated. Additional features of the invention will be described hereinafter. These form the subject of the claims of the invention. It should be appreciated by those skilled in the art that the conception and the disclosed specific embodiment may be readily utilized as a basis for modifying or designing other methods and structures for carrying out the same purposes of the present invention. It should also be realized by those skilled in the art that such equivalent methods and structures do not depart from the spirit and scope of the invention as set forth in the appended claims.

BRIEF DESCRIPTION OF THE DRAWINGS

For a more succinct understanding of the nature and objects of the invention, reference should be directed to the following description taken in conjunction with the accompanying drawings in which:

FIG. 5 is an exploded sectional view of the cuvette of FIG. 2.

FIGS. 6, 7, and 8 are sectional views of the cuvette illustrating its method of use.

FIG. 9 is an enlarged sectional view of one of the needles within the cuvette taken along line 9—9 of FIG. 5.

Similar reference numerals refer to similar parts throughout the several Figures.

DETAILED DESCRIPTION OF THE PREFERRED EMBODIMENT OF THE INVENTION

Figure 1:
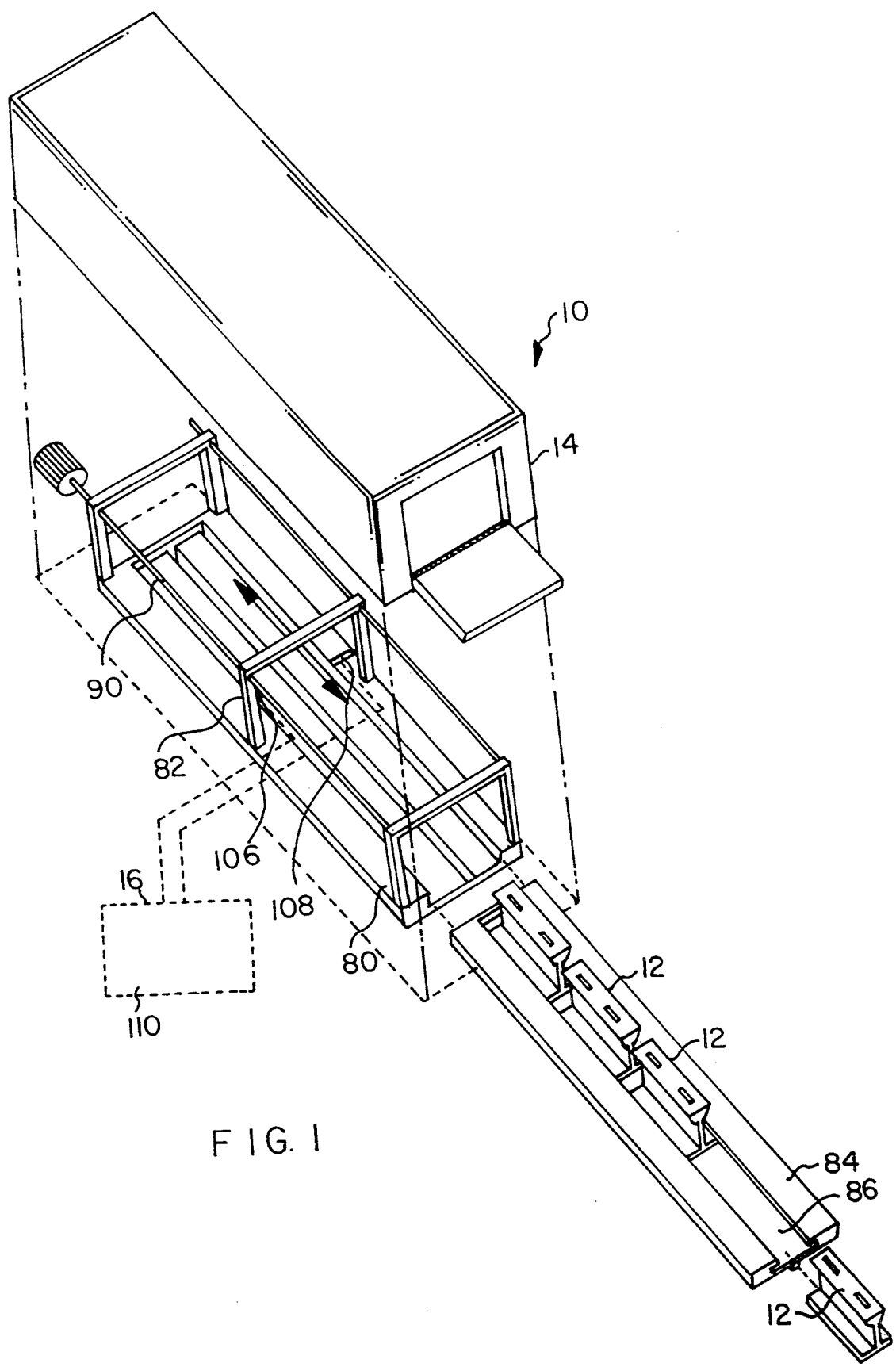
FIG. 1 is a perspective illustration of a blood analysis system constructed in accordance with the principles of the present invention and for carrying out the method of the present invention.
Figure 2:
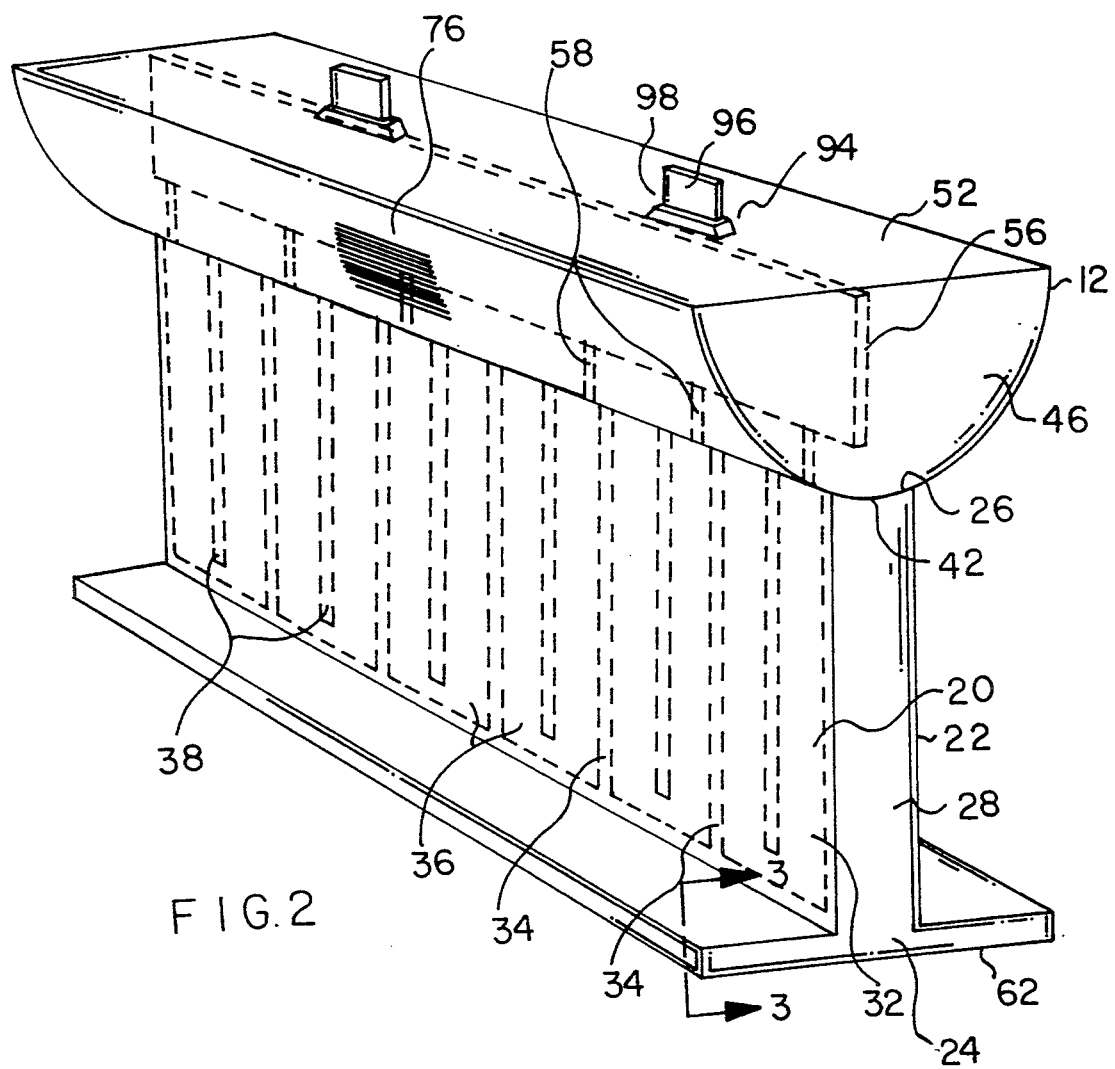
FIG. 2 is an enlarged perspective view of a cuvette constructed as shown in FIG. 1.

Shown in the Figures, with particular reference to FIG. 1, there is shown a blood analysis system 10 for analyzing a sample of blood for a plurality of characteristics and for carrying out the method of the present invention. The system, in its broadest of terms comprises, in combination, a plurality of cuvettes 12, a housing 14 and processing mechanisms 16.

A plurality of cuvettes 12 are first provided. Each cuvette has a front face 20, a rear face 22, a closed lower edge 24, an open upper edge 26 and parallel side walls 28 therebetween. The relationship provides a lower volume 32 therebetween. A plurality of long divider members 34 are located at spaced locations between the front and rear faces and top and bottom walls to divide up the cuvette into a plurality of separate chambers 36. Each chamber 36 has an intermediate short divider member 38 extending downwardly from the top of the upper edge to a location above the lower edge. This forms the chambers into essentially U-shaped chambers.

A first or lower horizontal sheet 42 extends across the spacers between the front and back faces and side walls. The chambers are thus separated one with respect to the other. Each chamber supports a vacuum with a different reagent 44 therein. A horizontal reservoir 46 is formed in each cuvette with a diluent 48. Such horizontal reservoir is located above the first horizontal sheet. A second or upper horizontal sheet 52 is located above the first horizontal sheet to form the horizontal reservoir 46 positioned to overlie the chambers 36.

Between the first and the second horizontal sheets is formed an intermediate plate 56 with downwardly directed pins 58 located at spaced points corresponding to the spaced chambers 36. As a result, downward movement of the plate 56 with its pins 58 at spaced points will puncture the first horizontal sheet 42 and allow the flow of fluid from the horizontal reservoir 46 into the vertical chambers for reacting with the reagents 44. An axial slot 60 in each pin allows for movement of the body fluid and diluent into the chambers.

The exterior surface of the upper horizontal chamber is flared outwardly to form the reservoir 46 for containing the diluent 48. A lower horizontal base 62 is provided for being supported by the processing machinery. The second horizontal sheet is also formed with a small aperture 64 and an associated stopper 66. The aperture and stopper are cooperatively tapered for better sealing. The purpose of the aperture and stopper is for allowing the addition of body fluids into the horizontal reservoir and for the subsequent movement thereof into the chambers 36 for analysis.

Figure 3:
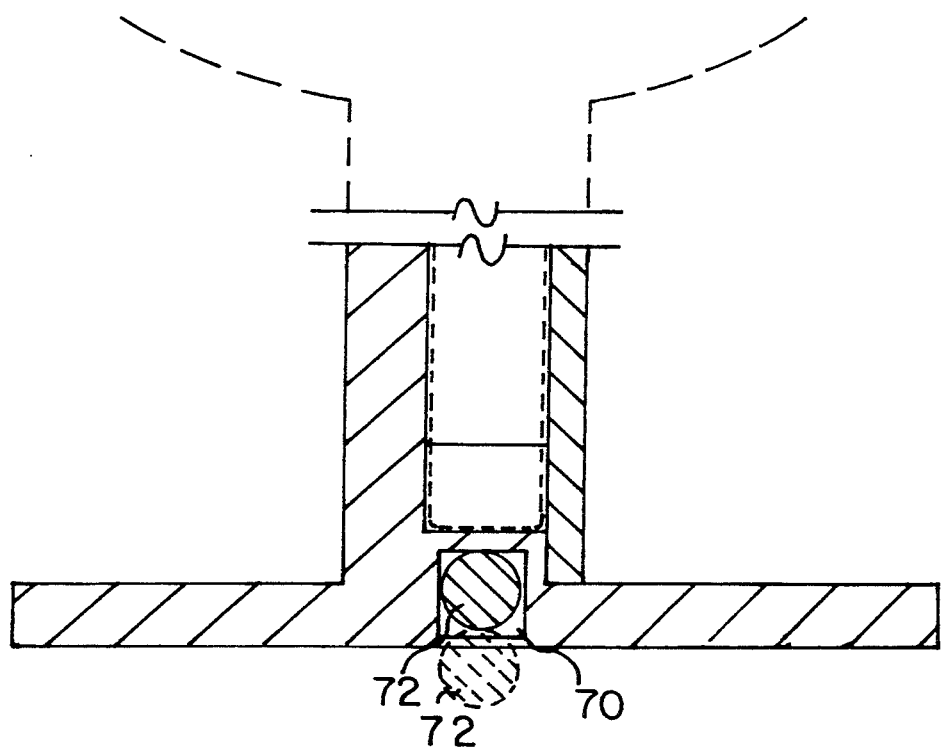
FIGS. 3 and 4 are sectional views taken along line 3—3 of FIG. 2 and line 4—4 of FIG. 3 respectively and showing the bottom of the cuvette illustrating the sealing of the chambers prior to use.
Figure 4:
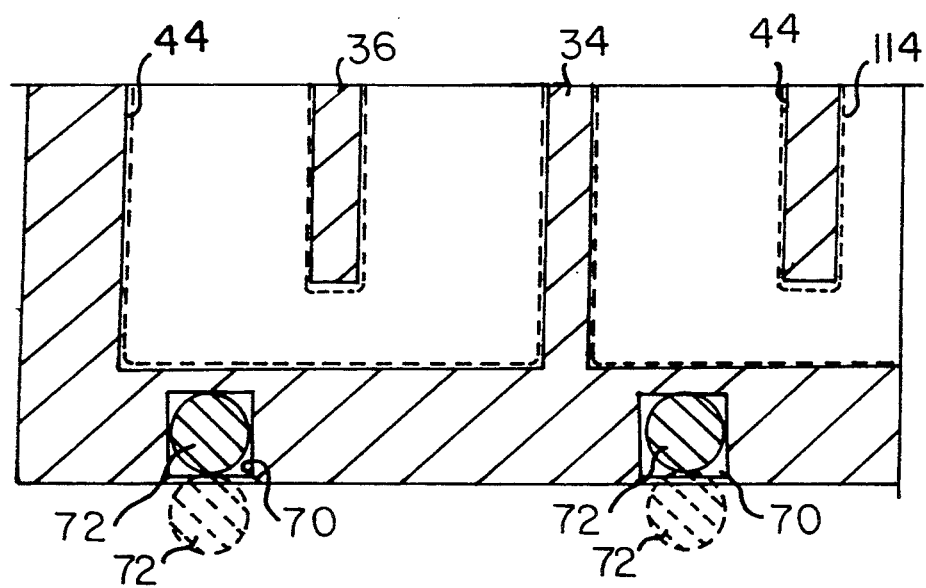

A lower face of each cuvette is initially provided with a small aperture 70 for use in introducing the reagents 44 into the chambers of the cuvette. One aperture is provided for each chamber. A reagent of a particular characteristic is injected to each chamber. The reagents thus injected can be freeze-dried or of liquid form. The vacuum is then applied. A stopper ball 72 is then inserted into the hole in a press fit configuration to maintain the chamber airtight with a vacuum therein and to ensure the sterility of the reagent and the chamber. Note FIGS. 3 and 4. Depending on the nature of the reagent in the particular chamber, a bar code 76 is provided on orate face of the cuvette for being read by the processor to ensure a proper analysis of the proper sample.

The second component of the system is the housing assembly 14. The housing assembly has a fixed frame 80 and a support subassembly 82 reciprocable with respect to the frame 80. The support subassembly 82 includes a fixed lower plate 84 with a recess 86 to receive the cuvettes and support them in edge-to-edge relationship in a linear array. Note FIG. 1. A lead screw 90 is coupled thereto through a threaded aperture to move the light source and detector with respect to the supported cuvettes in a reciprocable path of travel. The drive motor is not shown.

The third and last assembly of the system is the processing mechanisms 16. Such processing mechanisms 16 are associated with the housing assembly 14 and include first means 94 to drive the plate 56 and pins 58 downwardly to form holes 102 in the first horizontal sheet 42. Such driving down is effected by applying a downward force to upward extensions 96 of the plate 56. The extensions project upwardly through slots 98 in the upper sheet 52. Such force may be applied manually or by suitable mechanisms, not shown, operable by the computer. Compare FIGS. 6, 7 and 8. Holes 102 are thus located over each chamber 36. In this manner, body fluids, intermixed with the diluent in the horizontal reservoir 46, will be drawn into the chambers 36 for mixing with the reagents 44 to facilitate the analysis thereof.

The processing mechanisms further include a movable light source 106 and an associated concurrently movable sensor 108 located in an operative relationship with the light source on opposite sides of the path of travel of the cuvettes 12. Fixed computer means 110 are operatively associated with the sensor 108 to analyze and determine a plurality of characteristics of the fluids within the chambers, one characteristic for each chamber.

Multiple analyses can be performed in each individual chamber by placing multiple reagents 44 and 114 in any single chamber 36. Each reagent 44 absorbs light of a different wavelength in the same chamber. The detector imbodied in this invention is capable of measuring a large number of wavelengths of light, at present 1024 different wavelengths. By using appropriate mathematical equations, the complex spectrum produced by the multiple reagents can be reduced to individual concentrations of components of the body fluid analyzed. This technique can also be applied to any other solution such as drinking water, etc. to provide the same result.

Several other variations in the processing are available. For example, when the sample to be tested for certain characteristics, the reagent might be such as to make the sample flourescent, irridescent, phosphorescent, bioluminescent, light scattering or the like including environmental samples or other aqueous or non-aqueous solutions. In such situation, the light source and sensor could be provided on the same side of the path of travel of the light source and sensor with respect to the cuvettes. Further, it is also possible to use multiple fiber optic filaments and associated multiple fiber sensors for determining a plurality of characteristics of each chamber. In this regard, a large number of configurations of light sources and sensors could be utilized with associated computer programming as is well within the state of the art.

Although the invention herein has been disclosed as being carried in a medical laboratory environment, it should be realized that the invention is equally applicable to a wide range of materials to be tested as for example, the juices of plants as well as water and soil samples. Further, because of the use of vacuum to fill the cuvettes, there is no reliance on gravity for performing the process and as such process could be carried out in a gravity free environment.

The cuvettes may also be used in the testing for virals, fungi and bacterial growths within the biophied tissue. It can further be used in the detection of allergies, by allowing tissue cultures to grow within the confines of the cuvette. This will expose the excitation of the histamines that have been exposed within the culture.

The method of the present invention is for analyzing a sample of blood or other fluid for a plurality of characteristics and comprises various steps. The first step is providing a cuvette with a plurality of chambers for fluid to be analyzed. Further details of the cuvette are set forth hereinabove.

The next step is providing a housing assembly having a frame and a support subassembly reciprocable with respect to each other, the support subassembly including a base to receive the cuvette. Further details of the housing assembly are set forth hereinabove.

The next step is providing processing mechanisms associated with the housing assembly including first means to intermix the fluid with a diluent and then with reagents in the chambers to facilitate the analysis thereof, the processing mechanisms further including a light source and an associated sensor located in an operative relationship with respect to the cuvette and computer means operatively associated with the sensor to determine a plurality of characteristics of the fluid within the chambers. Further details of these components are set forth hereinabove.

The last step is effecting movement between the cuvette and the sensor while operating the light source and sensor whereby the computer means analyzes the sensed light from the sensor as modified by the fluid in the chambers. Further details of these components are set forth hereinabove.

A wide variety of sources are available for the reagents which are commercially available. By way of example, such sources include Sigma Chemical, Inc. of St. Louis, Mo.; Bio-Analytic Laboratories, Inc. of Palm City, Fla.; Fisher Scientific of Pittsburgh, Pa.; American Type Culture Collection of Rockville, Md.; and Hach Company of Loveland, Colo. The optical light source, detector and controlling software are also commercially available as from Ocean Optics, Inc. of Clearwater, Fla. while the computer is also commercially available as from SecureCom Technologies, Inc. of Clearwater, Fla.

The present disclosure includes that contained in the appended claims as well as that of the foregoing description. Although this invention has been described in its preferred form with a certain degree of particularity, it should be understood that the present disclosure of the preferred form has been made only by way of example and that numerous changes in the details of construction and combination and arrangement of parts may be resorted to without departing from the spirit and scope of the invention.

Now that the invention has been described,
What is claimed is:

1. A system for analyzing a sample of blood for a plurality of characteristics comprising, in combination:

a plurality of cuvettes, each cuvette having a front wall, a rear wall, a closed lower edge, an open upper edge and parallel side walls therebetween, thereby providing a lower space of a predetermined volume, a plurality of long divider members located at spaced locations between the front and rear walls and the upper and lower edges to divide up the cuvette into a plurality of separate chambers, each chamber having an intermediate short divider member extending downwardly from the upper edge to a location above the lower edge thereby forming the chambers into essentially U-shaped chambers, a first horizontal sheet extending across the divider members between the front and rear walls and side walls to seal the chambers one with respect to the other, each chamber supporting a vacuum with a different reagent therein, a second horizontal sheet above the first horizontal sheet to form a horizontal reservoir with a fluid diluent positioned between the horizontal sheets to overlie the chambers, a plate within the reservoir with downwardly directed pins at spaced points corresponding to the separated chambers whereby downward movement of the plate and pins will puncture the first horizontal sheet and allow the flow of fluid from the horizontal reservoir into the separated chamber for reacting with the reagents, the cuvette having a lower extent with a horizontal support for being retained by a base, the second horizontal sheet also being formed with a small aperture with an associated stopper for allowing the addition of body fluids into the horizontal reservoir for analysis;

a housing assembly having a fixed frame and a movable support subassembly reciprocable with respect to the frame, the frame including a base with a longitudinal slot for retaining said plurality of cuvettes in edge-to-edge relationship in a linear array and means to move the movable support subassembly with respect to the retained cuvettes in a linear path of travel; and processing means in the housing assembly including first means to drive the pins downwardly to form holes in the first horizontal sheet with a hole over each chamber whereby body fluids intermixed with diluent in the horizontal reservoir will be drawn into the chambers for mixing with the reagent to facilitate the analysis thereof, the processing means further including a movable fiber optic light source and an associated movable fiber optic sensor located in an operative relationship with the light source on opposite sides of a path of travel and fixed computer means operating with the sensor to determine a plurality of characteristics of the fluids within the chambers, one characteristic for each chamber.

2. A cuvette for use in analyzing a sample of blood for a plurality of characteristics comprising a front wall, a rear wall, a closed lower edge, an open upper edge and parallel side walls therebetween, thereby providing a lower space of a predetermined volume, a plurality of long divider members located at spaced locations between the front and rear walls and the upper and lower edges to divide up the cuvette into a plurality of separate chambers, each chamber having an intermediate short divider member extending downwardly from the upper edge to a location above the lower edge thereby forming the chambers into essentially U-shaped chambers, a first horizontal sheet extending across the spacers between the front and rear walls and side walls to seal the chambers one with respect to the other, each chamber having therein a vacuum with a different reagent therein, a second horizontal sheet above the first horizontal sheet to form a horizontal reservoir with a fluid diluent positioned between the horizontal sheets to overlie the chambers, a plate within the reservoir with downwardly directed pins at spaced points corresponding to the separated chambers whereby downward movement of the plate and pins will puncture the first horizontal sheet and allow the flow of fluid from the horizontal reservoir into the separated chambers for reacting with the reagents, the cuvette having a lower extent with a horizontal support for being retained by a base, the second horizontal sheet also being formed with a small aperture with an associated stopper for allowing the addition of body fluids into the reservoir for analysis.

* * * * *